United States Patent [19]

Boehringer

[11] 4,004,585
[45] Jan. 25, 1977

[54] SAFETY INTERFACE FOR ANESTHESIA VACUUM SCAVENGING

[76] Inventor: John R. Boehringer, 427 Parkview Drive, Wynnewood, Pa. 19096

[22] Filed: Nov. 18, 1975

[21] Appl. No.: 632,894

[52] U.S. Cl. .............................. 128/145.8; 128/188
[51] Int. Cl.² .................................... A61M 16/00
[58] Field of Search ............ 128/188, 145.8, 145.6, 128/142 R, 142.3, 276; 137/312

[56] References Cited

UNITED STATES PATENTS

| | | | |
|---|---|---|---|
| 3,467,094 | 9/1969 | Goodman | 128/142 R |
| 3,646,935 | 3/1972 | Holbrook et al. | 128/276 |
| 3,721,239 | 3/1973 | Myers | 128/188 |
| 3,800,793 | 4/1974 | Marrese et al. | 128/188 |
| 3,865,106 | 2/1975 | Palush | 128/188 |
| 3,924,618 | 12/1975 | Banjavich et al. | 128/142.3 |

*Primary Examiner*—Robert W. Michell
*Assistant Examiner*—Henry J. Recla
*Attorney, Agent, or Firm*—Paul & Paul

[57] ABSTRACT

Gases from a pressure relief valve in the patient circle are coupled to a first end of an elongated rigid cylinder, the other end of which is coupled to a vacuum exhaust pump. Coaxially disposed within the cylinder is an elongated tube which deposits gases from the valve to within a predetermined distance of the vacuum withdrawal port of the cylinder. The cylinder defines openings to ambient air at the first side, and baffling material is provided at the vacuum withdrawal end to facilitate intermixing of gas and air and prevent gas splashing.

8 Claims, 2 Drawing Figures

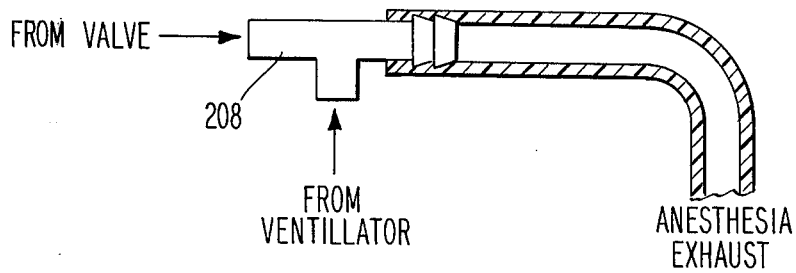
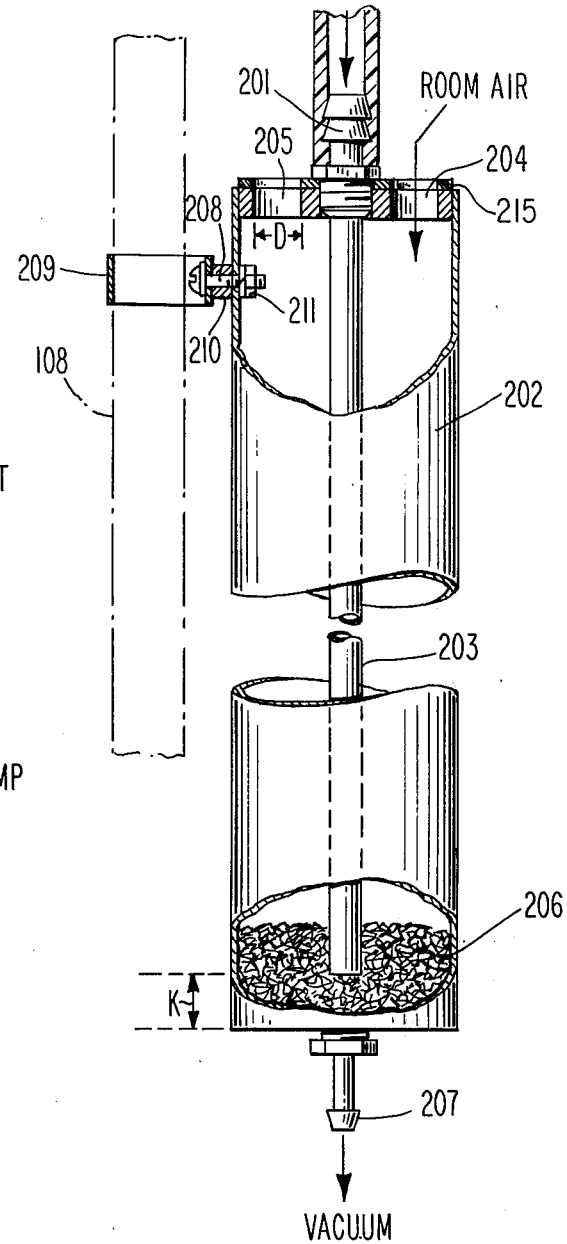
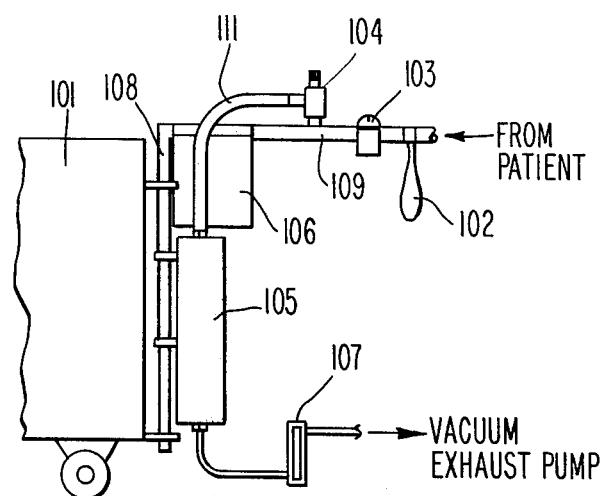

SAFETY INTERFACE FOR ANESTHESIA VACUUM SCAVENGING

BACKGROUND OF THE INVENTION

This invention relates to apparatus for the administration of anesthesia, and more particularly to safety apparatus for facilitating removal of anesthetic gases safely from the operating area.

A conventional method for administration of gaseous anesthesia features the so-called patient anesthesia circle, wherein oxygen and the anesthetic gases are coupled to the patient for inhalation, and exhaled gases are passed through a carbon dioxide absorber and back to the entry point of oxygen and anesthesia. One way valves isolate the patient from the source of anesthesia and the carbon dioxide absorber, and a reservoir bag is provided on the patient's side of the valves. In such a system, it is important to provide apparatus in the circle to prevent pressure build ups which may be harmful or fatal to the patient. To this end, pressure relief valves conventionally are included, which are designed to open the system to the atmosphere when pressure exceeds a predetermined threshold. The most common designs of such valves feature diaphragms or pistons which are held in place by the force of a spring. When pressure in the circle is sufficient to deflect the spring, the diaphragms or pistons are displaced, and pressure is relieved.

In a co-pending application of John R. Boehringer, Ser. No. 609,072 filed Aug. 29, 1975 and entitled "Pressure Relief Valve for Anesthetic Administration," there is disclosed a type of valving apparatus which provides safe and reliable pressure relief for the patient circle, and which also is amenable to systems wherein anesthesia gases expelled from the patient circle are safely removed from the operating area, such as by means of vacuum pumps. That development reflects the attention recently given to the fact that operating room personnel often are undesirably exposed to anesthetic gases which are permitted randomly to enter the ambient atmosphere. Vacuum exhaust systems, also known as scavenging systems, have been devised for removal of the gases prior to their introduction in the operating room atmosphere.

Although the vacuum systems currently developed do an adequate job of removing the anesthetic gases from the patient circle, they also have tended undesirably to endanger the patient. That is, unless safety interface apparatus is provided intermediate the vacuum pump and the anesthetic circle pressure relief valve, there exists the possibility that a vacuum will be applied directly to the patient's lungs during malfunction or misuse of the various anesthesia administration devices.

It is a primary object of the present invention to provide safety interface apparatus for exhausting anesthetic gases from the patient circle without exposing the patient to direct vacuum application.

It is a further object that the safety interface so provided affords an access to ambient air whereby positive pressure build up in the line, such as may be caused during inadvertent exhaust line occlusion, will not be passed on to the patient.

Another common application in anesthesia administration in the use of reservoir bags in the patient circle which provides a reservoir, and also allows the anesthesiologist to provide predetermined back pressure to the patient by squeezing the bag (i.e., commonly known as "bagging" the patient). It is a further object of the present invention to provide a storage reservoir capacity whereby ventilation exhausts created by bagging may be relieved without causing excessive pressure in the system due to pressure drop in the vacuum exhaust circuit.

SUMMARY OF THE INVENTION

The present invention involves apparatus intermediate the vacuum exhaust pump and the pressure relief valve of the patient circle. The scavenger safety interface so provided inserts a discontinuity in the vacuum line between the pump and the pressure relief valve, but obviates the possibility of expulsion of anesthetic gases into the ambient operating area. In particular, an elongated rigid cylinder encloses the discontinuity, and provides for receipt of gases from the anesthetic circle pressure relief valve at one end. The vacuum exhaust withdraws gases from the other end. Within the cylinder, and preferably coaxially therewith, a tube carries received gases from the valve to within a predetermined distance of the vacuum exhaust. Openings in the cylinder near the gas receipt point provide for introduction of room air, and baffling material in the area of the discontinuity provides safe intermixing of gases and air, and avoidance of "splash back" effects which may arise due to surges in pressure.

DESCRIPTION OF THE DRAWINGS

FIG. 1 shows an illustrative interconnection of an embodiment of the principles of the present invention with conventional anesthesia administration equipment; and FIG. 2 shows in partial cutaway a preferred embodiment of the principles of the present invention.

DETAILED DESCRIPTION

In FIG. 1, a conventional anesthesia machine is presented at 101, with a standard carbon dioxide absorber support pipe 108 affixed thereto. The carbon dioxide absorber within the support 108 functions conventionally with the patient anesthetic circle apparatus including sources of oxygen and anesthetic gases at 106, the closed system to and from the patient 109, and appropriate check valves 103 in the circle. A storage reservoir bag 102 is provided on the patient's side of the check valve 103 of the exhalation branch of the circle. The bag 102 serves conventionally to capture peak exhaust surges, and also permits the anesthesiologist to exert back pressure against the patient to the extent clinically desired. A pressure relief valve 104, advantageously of the type set forth in the above reference co-pending application of John R. Boehringer, is provided to open the patient circle 109 whenever the pressure therein exceeds certain predetermined levels.

As shown in FIG. 1, the outlet of the valve 104 is passed through convenient tubing 111 to a safety interface 105 embodying the principles of the present invention, and thence to a vacuum exhaust pump, not shown, through a suction flow meter 107. The meter 107 allows continuous monitoring of system functions, and also permits calibration of the interface 105 as set forth hereinafter.

FIG. 2 shows a preferred embodiment of the present invention. In FIG. 2, an elongated rigid metallic cylinder 202 is mounted by appropriate bolt 208, collar 209, flexible washer 210, and nut and lock washer 211 to the absorber support pipe 108. The lower end of the cylinder 202 is sealed except for an exhaust port communicating with a hose fitting 207, whereby the interconnection to the vacuum exhaust apparatus may be made such as shown in FIG. 1. The top portion of the cylinder 202 also provides a hose fitting 201, whereby anesthesia exhaust gases from the patient circle are provided. The top of the cylinder defines openings such as 204 and 205 whereby the interior cavity of the cylinder 202 freely communicates with ambient room air. As set forth hereinafter, the flow of room air is generally into the cylinder, for withdraw by the vacuum via 207. However, the openings 204 and 205 do provide an emergency exhaust port for the cylinder, in the case of occlusion somewhere in the system. A damper means 215 optionally is included for varying the effective size of openings 204 and 205.

An elongated rigid tube 203 receives the anesthesia exhaust gases from the patient circle and deposits them a predetermined distance, K, away from the vacuum exhaust port of the cylinder 202. Hence, the vacuum pulls at the lower port 207, and gases from the patient circle may be received at rates greater or less than the suction rate. The cylinder 202 provides a reservoir for peak flows, and ambient air is drawn in during low flow or no flow times. Depending on the size D of the openings 204 and 205, the length of the discontinuity K, the capacity of the cylinder 202, and the vacuum suction rate, a predetermined calibrated pressure is exerted upon the patient anesthesia circle via the valve 104.

As shown in FIG. 2, the anesthesia exhaust to the cylinder inlet 201 is coupled from a tee connection 208, one input of which comes from the valve 104, and another comes from a ventilator, not shown, interconnected with the reservoir bag 102. Such ventilation systems are conventional, and are utilized in conjunction with the bag 102 when exerting back pressure against the patient.

In a preferred embodiment, the cylinder 202 is 23 inches in length, 3 inches in diameter, and has a total capacity of 2.0 liters. The openings such as 204 and 205 at the top of the cylinder 202 have a total area of 0.88 inches squared, and the preferred distance K between the end of tube 203 and the bottom of cylinder 202 is 0.500 inches. Such a configuration easily and safely handles a suction flow of 20 to 30 liters per minute. The cylinder itself 202 and the tube 203 advantageously are composed of aluminum.

As shown in FIG. 2, the area of the discontinuity between the anesthesia exhaust via tube 203, and the vacuum exhaust via 207, is occupied with a crushed flow baffle material 206, advantageously crushed copper mesh. The baffle 206 breaks up the flow of gases from the tube 203 and from the inlets 204 and 205, and likewise prevents a splashing effect which may occur due to sudden surges in exhaust from the tube 203, which otherwise might force anesthesia gases back out into the room.

The foregoing is submitted as illustrative of the principles of the present invention, but it is to be understood that numerous alternative embodiments will occur to those of ordinary skill in the art without departure from the spirit or scope of the present invention.

I claim:

1. In an anesthesia administration system having pressure relief valving in the patient circle and a vacuum exhaust from the valving, safety interface apparatus comprising:

an elongated cylindrical means having an interconnection with said vacuum exhaust at one end and an interconnection with said valving at its other end, said cylindrical means being closed to atmosphere at said one end and defining openings at said other end to allow free passage of ambient air into said means;

an elongated tubular means within said cylindrical means, said tubular means being connected to receive gases from said valving via said interconnection at said one end, said tubular means terminating with an opening a predetermined distance from said one end; and baffle means within said cylindrical means at said one end and occupying at least a portion of said predetermined distance between said one end and the termination of said tubular means for preventing a splashing effect which may occur due to sudden surges of exhaust gases from said valve means.

2. Apparatus as described in claim 1 wherein said baffle means comprises copper mesh material substantially randomly packed within said one end.

3. Apparatus as described in claim 2 wherein said baffle means is packed throughout said predetermined distance, and extending away from said one end beyond said termination of said tubular means.

4. Apparatus as described in claim 1 wherein said tubular means is substantially coaxial within said cylindrical means, said interconnection with said valving is located substantially on said axis, and said openings are disposed substantially radially around said interconnection with said valving.

5. Apparatus as described in claim 4 wherein said cylindrical means is substantially vertically disposed with said one end at the bottom and said other end at the top.

6. Apparatus as described in claim 1 and further including an adjustably opening damper means for varying the effective size of said openings.

7. Apparatus as described in claim 1 and further including a three opening tee interconnection having a first opening coupled to said tubular means via said interconnection at said other end, a second opening coupled to said valving, a reservoir bag, said tee interconnection having a third opening connected to said reservoir bag in the patient circle.

8. Vacuum scavenging apparatus for anesthesia administration systems comprising:

pressure relief valving means opening to the patient administration circle at a predetermined pressure;

a rigid elongated cylinder having means at one end for receiving gases from said valving means, and for expelling gases at its other end, said cylinder being closed to atmosphere at said other end and defining openings at said one end whereby its interior chamber communicates with its ambient atmosphere;

an elongated tubular means extending within said cylinder from said one end to within a predetermined distance of said other end for conveying gases received from said valving means to the interior of said cylinder;

baffle means within said cylinder at said other end for preventing a splashing effect which may occur due to sudden surges of exhaust gases from said valve means; and a vacuum exhaust pump means for withdrawal of gases from said cylinder at said other end.

* * * * *